United States Patent [19]

Svirklys

[11] 4,194,320
[45] Mar. 25, 1980

[54] PLANT GROWING UNIT

[75] Inventor: Ferdinand M. Svirklys, Toronto, Canada

[73] Assignee: Extrados Company Limited, Toronto, Canada

[21] Appl. No.: 895,342

[22] Filed: Apr. 11, 1978

[30] Foreign Application Priority Data

Apr. 13, 1977 [GB] United Kingdom ............... 15416/77

[51] Int. Cl.² .................... A01G 9/00; A01K 67/00
[52] U.S. Cl. ............................. 47/59; 119/15
[58] Field of Search ................. 119/1, 15, 16; 47/59, 47/17, 19, 48.5, 60, 61

[56] References Cited

U.S. PATENT DOCUMENTS

| | | | |
|---|---|---|---|
| 94,169 | 8/1869 | Jillson | 47/19 |
| 1,948,031 | 2/1934 | Guille | 47/79 |
| 2,026,322 | 12/1935 | Raines | 47/61 |
| 2,993,300 | 7/1961 | Sawyer | 47/61 |
| 3,635,816 | 1/1972 | Golub | 119/1 X |
| 3,654,903 | 4/1972 | Montgomery | 47/17 X |
| 3,894,355 | 7/1975 | Carothers | 47/48.5 |
| 3,961,603 | 6/1976 | Gaddie | 119/15 |
| 4,077,158 | 3/1978 | England | 47/17 |

Primary Examiner—Paul T. Sewell
Assistant Examiner—James R. Feyrer
Attorney, Agent, or Firm—Sim & McBurney

[57] ABSTRACT

A plant growing unit comprises a plant growing portion and a fertilizer-producing portion containing earthworms. The earthworms produce the fertilizer from vegetable matter and the fertilizer is used for growing the plants, preferably by the hydroponic technique. In a preferred embodiment, the fertilizer-producing portion is constructed also to permit the behavioral pattern of the worms to be observed.

5 Claims, 2 Drawing Figures

PLANT GROWING UNIT

FIELD OF INVENTION

The present invention relates to a plant growing unit.

SUMMARY OF INVENTION

A plant growing unit in accordance with this invention comprises a plant-growing portion and a fertilizer-producing portion containing earthworms. In a preferred embodiment of the invention, the fertilizer-producing portion is constructed to permit the behavioural patterns of worms to be observed.

DESCRIPTION OF PREFERRED EMBODIMENTS

Figure 1:
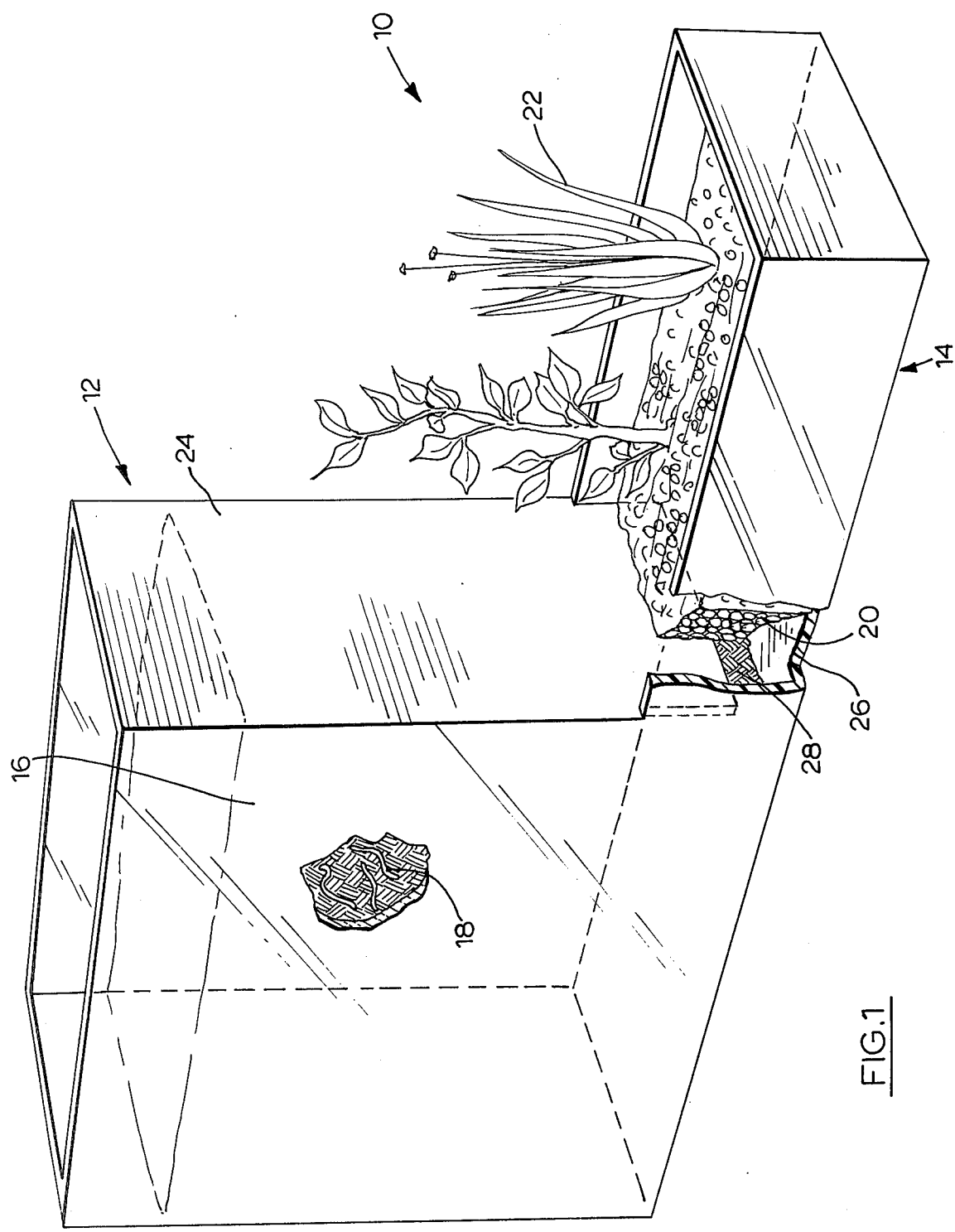
FIG. 1 is a perspective view, with parts cut away, of a plant growing unit, provided in accordance with one embodiment of the invention.

Referring to the drawings, in FIG. 1 there is illustrated a plant-growing unit 10 constructed in accordance with one embodiment of the invention. In this embodiment, the unit comprises a box-like container portion 12 having an open top and a shallow tray portion 14 also having an open top and joined to the container portion 12.

The container portion 12 is constructed of transparent glass or clear rigid plastic material and contains a bed of soil 16 in which earthworms 18 are located. The tray portion 14 is constructed of glass, plastic material, or any other convenient construction material and may be transparent or opaque. Usually, the container portion 12 and the tray portion 14 are constructed of the same material for ease of manufacture. The tray portion 14 takes the form of a small garden consisting of a bed of gravel 20 in which plants 22 of any desired type are growing by the hydroponic technique.

If desired, the tray portion 14 may contain a bed of soil in place of the gravel 20, although this may result in unwanted migration of the worms 18 from the soil bed 16.

The side wall 24 of the container portion 12 facing the tray portion 14 does not extend the full height of the container portion 12 but rather terminates at its lower end at a location spaced from the bottom wall 26 which extends the whole length of the unit 10 to define a transverse slot-like opening 28 therebetween, thereby establishing liquid flow communication between the interiors of the container portion 12 and the tray portion 14.

Earthworms are capable of converting vegetable matter, including waste vegetable matter, into high grade plant fertilizer. The container portion 12 of the unit 12 is used for the formation of such high grade plant fertilizer from vegetable matter placed in the container portion 12, by the action of the worms 18.

When liquid is required by the hydroponic garden in the tray portion 14, water is poured into the container portion 12. The water dissolves the worm castings, containing the high grade fertilizer, as it percolates through the soil bed 16 and enters the tray portion 14 through the slot 28 carrying with it the high grade fertilizer to the gravel 20, thereby fertilizing and dampening the roots of the plants 22 growing in the gravel 20.

Plants grown in the tray portion 14, such as, from seeds or seedlings, may be used as the feed of vegetable matter to the container portion 12, to form fertilizer for further plants. If the plants 22 are those that produce seeds, then the life cycle within the plant growing unit 10 of growing seeds to grown plants and using the plants to produce fertilizer for more plants is self-sustaining, requiring only an external water requirement.

The fertilized soil in the bed 16 may be used for plantings in other convenient soil-containers, such as, plant pots or the like, the fertilized soil so removed being replaced by unfertilized soil.

Figure 2:
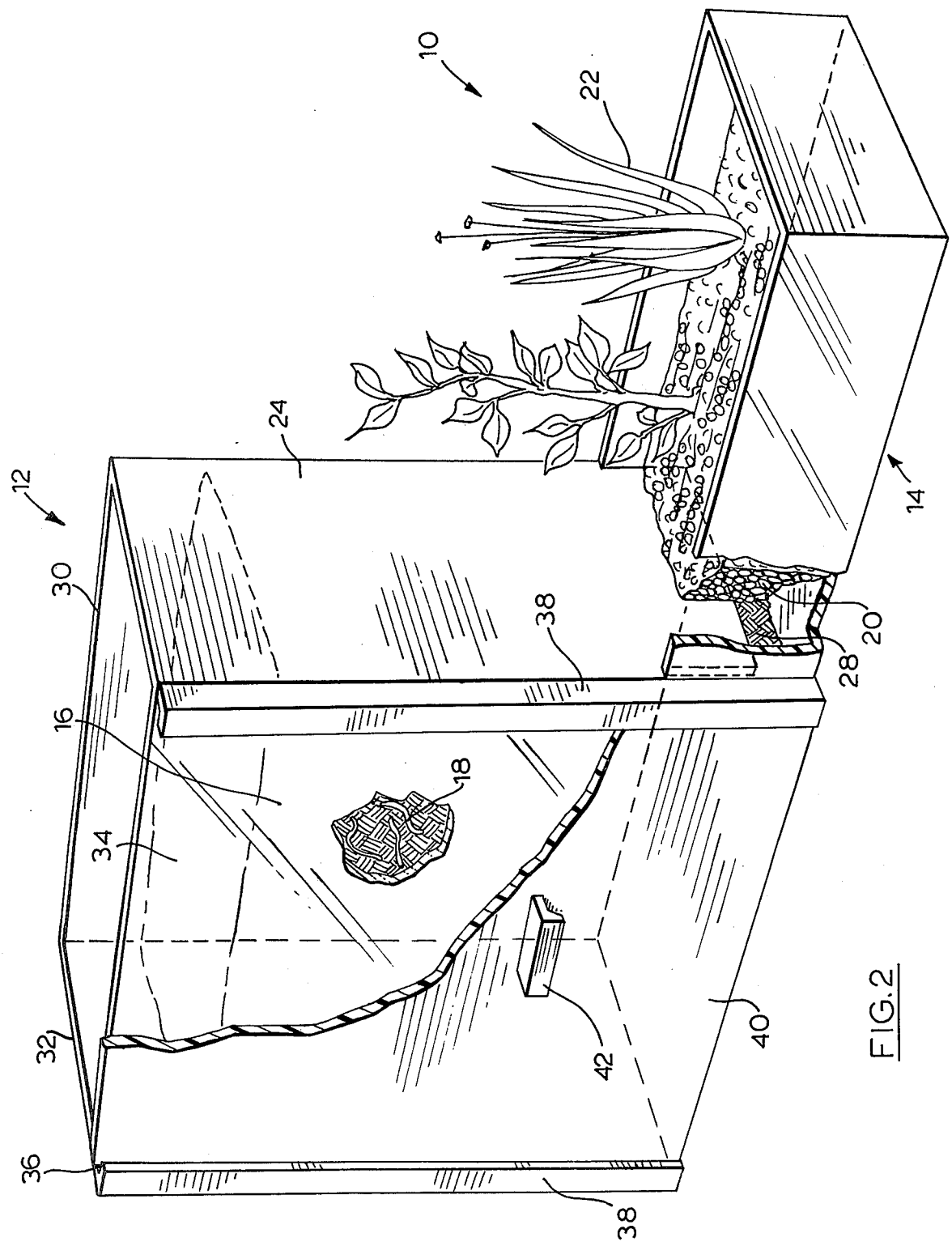
FIG. 2 is a perspective view, with parts cut away, of a modified plant growing unit, provided in accordance with a second embodiment of the invention.

A modification of the structure of unit 10 is shown in FIG. 2, and common reference numerals are used to designate the same parts in the two Figures. The modification to the structure of FIG. 1 which is illustrated in FIG. 2 relates to the structure of the container portion 14.

The walls 24, 30 and 32 on three sides of the container portion 14 are constructed of opaque material so that light cannot enter the soil bed 16 through those walls while the wall 34 on the fourth side is transparent.

A pair of vertically-extending channels 36 are defined by vertical flange elements 38 jointed to the transparent wall 34 and extending the whole height of the wall 34.

A sheet of opaque material 40 is slidably received in the channels 36 and covers the transparent wall 34. The opaque sheet 40 may be lifted, such as, by a handle 42 affixed to the outer face, to expose the transparent wall 34. The opaque sheet 40 is preferably received in friction fit engagement with the channels 36 to permit the opaque sheet 40 to be maintained in a raised position, if desired, by friction only. The opaque sheet 40 may be constructed of any convenient opaque material, including plastic, glass or metal.

The structure of the container unit 14 in the embodiment of FIG. 2 permits the behavioural pattern of worms to be observed in addition to processing the properties of the FIG. 1 structure.

Earthworms are repelled by light, so that, in the FIG. 1 structure, the worms burrow into the soil bed 16 away from the container walls and usually are not seen. Since the walls of the container portion 12 are normally opaque, with the opaque sheet 40 lowered, there is no such repellance in the FIG. 2 structure.

Worms are attracted by cool temperatures and moisture. As a result of the thermal conductivity of the material of construction of the walls 24, 30, 32 and 34 the inner surface of the walls tends to be cooler than the soil bed 16 and moisture condenses there. These results attract the worms 18 to the inside surface of the walls and the net effect is for the worms to congregate adjacent the walls and to carry out their natural behavioural patterns in this region.

The structure of FIG. 2 enables these patterns to be observed, by raising the opaque sheet 40 to expose the transparent wall 34 and the worms located adjacent thereto. When the opaque sheet 40 is lifted, the worms react to the light and tend to burrow away from the wall 34. Their movements are slow, however, and can readily be observed. Other activities of the worms, such as, eating also may be observed. The behavioural patterns so revealed are interesting and educational. These patterns are not normally observable owing to the living environment of the earthworms but this invention overcomes that difficulty.

Upon lowering of the opaque sheet 40 to again shut off the light, the worms return to the wall 34.

While the embodiment of FIG. 2 is illustrated as utilizing a single transparent wall 34 with associated reciprocable opaque sheet 40, it is possible within the scope of this invention to provide such a combination for any or all of the other side walls 24, 30 and 32.

The dimensions of the plant growing unit 10 may vary widely from a small portable size to a large scale permanent installation.

SUMMARY

The present invention, therefore, relates to a plant growing unit of unique structure, which may also be used to observe the behavioural pattern of worms. Modifications are possible within the scope of the invention.

What I claim is:

1. An integrally-formed plant growing unit constructed of transparent material, comprising
   a soil container portion housing a bed of soil adapted to have earthworms living therein,
   a hydroponic tray portion, containing gravel, joined to said soil container portion and adapted to have plants growing therein, and
   means establishing a liquid flow communication between said bed of soil and the nutrient medium sustaining said plants,
   said unit including an elongate bottom wall part of the length of which constitutes the bottom wall of said container portion and the remainder of the length of which constitutes the bottom wall of said tray portion, upstanding substantially parallel end walls one extending to a greater height than the other, said one wall constituting the end wall of said container portion and said other wall constituting the end wall of said tray portion, upstanding substantially parallel side walls, part of the length of which extend to the height of said one end wall and constitutes the side walls of said container portion and the remainder of the length of which extend to the height of said other end wall and constitute the side walls of said tray portion, and divider wall means separating said container portion from said tray portion and extending downwardly parallel to said end walls from the height of said one end wall to a location spaced from said bottom wall and below the height of said other end wall to define an unobstructed slot between the lower end of said divider wall means and said bottom wall constituting said means establishing fluid flow communication.

2. A plant growing unit, comprising
   a soil container portion housing a bed of soil adapted to have earthworms living therein,
   a hydroponic tray portion, containing gravel, joined to said soil container portion and adapted to have plants growing therein, and
   means establishing a liquid flow communication between said bed of soil and the nutrient medium sustaining said plants,
   said unit including an elongate bottom wall part of the length of which constitutes the bottom wall of said container portion and the remainder of the length of which constitutes the bottom wall of said tray portion, upstanding substantially parallel end walls one extending to a greater height than the other, said one wall constituting the end wall of said container portion and said other wall constituting the end wall of said tray portion, upstanding substantially parallel side walls, part of the length of which extend to the height of said one end wall and constitutes the side walls of said container portion and the remainder of the length of which extend to the height of said other end wall and constitute the side walls of said tray portion, and divider wall means separating said container portion from said tray portion and extending downwardly parallel to said end walls from the height of said one end wall to a location spaced from said bottom wall and below the height of said other end wall to define an unobstructed slot between the lower end of said divider wall means and said bottom wall constituting said means establishing fluid flow communication,
   at least one of said side and end walls of said container portion being transparent and being provided with removable opacifying means and any remainder of said walls are opaque.

3. The unit of claim 1 wherein said plants grow hydroponically in said gravel wet by said nutrient medium.

4. The unit of claim 1 wherein said removable opacifying means comprises an opaque sheet member movable into and out of opacifying relationship with said transparent wall.

5. The unit of claim 4 wherein said opaque sheet member is vertically slidably mounted in channel means to achieve said movement.

* * * * *